(12) United States Patent
Plata-Salaman et al.

(10) Patent No.: US 6,815,464 B2
(45) Date of Patent: Nov. 9, 2004

(54) CARBAMATE COMPOUNDS FOR USE IN THE TREATMENT OF PAIN

(75) Inventors: Carlos R. Plata-Salaman, Ambler, PA (US); Boyu Zhao, Lansdale, PA (US); Roy E. Twyman, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/081,943

(22) Filed: Feb. 21, 2002

(65) Prior Publication Data

US 2002/0156127 A1 Oct. 24, 2002

Related U.S. Application Data

(60) Provisional application No. 60/271,888, filed on Feb. 27, 2001.

(51) Int. Cl.[7] ............................................. A61K 31/27
(52) U.S. Cl. ...................... 514/483; 514/484; 514/489
(58) Field of Search ............................... 514/483, 484, 514/489

(56) References Cited

U.S. PATENT DOCUMENTS

| | | |
|---|---|---|
| 3,265,728 A | 8/1966 | Bossinger et al. |
| 3,278,380 A | 10/1966 | Bossinger et al. |
| 6,103,759 A | 8/2000 | Choi et al. |

FOREIGN PATENT DOCUMENTS

| | | |
|---|---|---|
| WO | WO 02/07822 A2 | 1/2002 |

OTHER PUBLICATIONS

U.S. patent application Ser. No. 09/906,251.
U.S. patent application Ser. No. 10/081,501.
U.S. patent application Ser. No. 10/081,766.
U.S. patent application Ser. No. 10/081,606.
U.S. patent application Ser. No. 10/081,761.
U.S. patent application Ser. No. 10/081,713.
U.S. patent application Ser. No. 10/193,600.
U.S. patent application Ser. No. 10/192,973.
U.S. patent application Ser. No. 10/081,764.
Search Report for PCT/US 02/05421 dated Jul. 1, 2002.
Ettore B.; The Use of Anticonvulsants in Neurological Conditions Other than Epilepsy: A Review of the Evidence from Randomized Controlled Trials; CNS Drugs, 1999; pp. 61–81; vol. 11, No.1.

Hansen, H. C.; Treatment of Chronic Pain with Antiepileptic Drugs: A New Era; Southern Medical Journal: Jul. 1999; pp. 642–649: vol. 92, No. 7.

Magnus, L.; Nonepileptic uses of Gabapentin: Epilepsia: 1999: pp. S66–S72; vol. 40 [Suppl. 6]; Lippincott Williams & Wilkins, Philadelphia.

Swerdlow, M.; Anticonvulsant Drugs and Chronic Pain; Clinical Neuropharmacology, 1984: pp. 51–82; vol. 7, No. 1: Raven Press, New York.

Wileman, L.; Advances in Pain Management: Scrip Report; Feb. 28, 2000: PJB Publications, Ltd.

*Primary Examiner*—Dwayne Jones
(74) *Attorney, Agent, or Firm*—Peter Herridge

(57) ABSTRACT

This invention is directed to a method for the treatment of pain comprising administering to a subject in need thereof a therapeutically effective amount of a compound selected from the group consisting of Formula (I) and Formula (II):

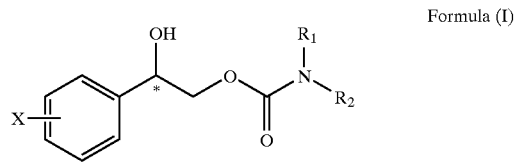

Formula (I)

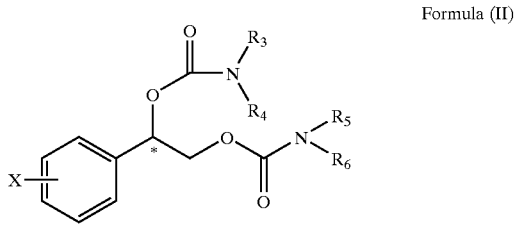

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

27 Claims, No Drawings

CARBAMATE COMPOUNDS FOR USE IN THE TREATMENT OF PAIN

CROSS REFERENCE TO RELATED APPLICATIONS

This application claims benefit of provisional application Ser. No. 60/271,888, filed Feb. 27, 2001, which is hereby incorporated by reference.

FIELD OF THE INVENTION

This invention is directed to a method for use of a carbamate compound in the treatment of pain. More particularly, this invention is directed to a method for use of halogenated 2-phenyl-1,2-ethanediol monocarbamate or dicarbamate compounds for the treatment of pain.

BACKGROUND OF THE INVENTION

Pain is generally defined as an unpleasant sensory and emotional experience, associated with actual or potential tissue damage (Wileman L, Advances in pain management, *Scrip Report*, 2000).

Acute pain is a physiological response to an adverse chemical, thermal or mechanical stimulus that may be associated with surgery, trauma or acute illness. These conditions include, but are not limited to, post-operative pain, sports medicine injuries, carpal tunnel syndrome, burns, musculoskeletal sprains and strains, musculotendinous strain, cervicobrachial pain syndromes, dyspepsia, gastric ulcer, duodenal ulcer, kidney stone pain, gallbladder pain, gallstone pain, dysmenorrhea, endometriosis, obstetric pain, rheumatological pain or dental pain.

Chronic pain is a pain condition beyond the normal cause of an injury or illness and may be a consequence of inflammation or serious, progressive, painful disease stages. Various types of chronic pain include, but are not limited to, headache, migraine, trigeminal neuralgia, temporomandibular joint syndrome, fibromyalgia syndrome, osteoarthritis, rheumatoid arthritis, bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy)), pelvic pain, cardiac chest pain, non-cardiac chest pain, spinal cord injury-associated pain, central post-stroke pain, cancer pain, AIDS pain, sickle cell pain or geriatric pain.

Anticonvulsants have been effectively used for treating pain since 1940 when phenytoin, originally used for epilepsy, was demonstrated to have beneficial effects on trigeminal neuralgia. It has been well documented that carbamazepine, clonazepam, valproic acid, gabapentin, lamotrigine and topiramate, originally developed as anticonvulsants for treating epilepsy, have all shown efficacy for various chronic pain conditions including trigeminal, glossopharyngeal, superior-laryngeal and post-herpetic neuralgia, tabetic pain, phantom limb pain, prophylaxis of migraine, multiple sclerosis, thalamic syndrome, diabetic neuropathy and neuropathic pain (Swerdlow M, Anticonvulsant drugs and chronic pain, *Clin. Neuropharmacol.*, 1984, 7, 51–82; Ettore B, The use of anticonvulsants in neurological conditions other than epilepsy: A review of the evidence from randomized controlled trials, *CNS Drugs*, 1999, 11, 1, 61–82; Leslie M, Nonepileptic uses of gabapentin, *Epilepsia*, 1999, 40 (Suppl. 6), S66–S72; Hansen HC, Treatment of chronic pain with antiepileptic drugs: a new era, *Southern Medical Journal*, 1999, 92, 7, 642–9). Anticonvulsants reduce excitability of neurons via their neurostabilizing properties, which may contribute to their efficacy in treating pain, since pain impulses are transmitted from nociceptors to the cerebral cortex via specific pathways throughout the spinal cord, brain stem and thalamus.

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

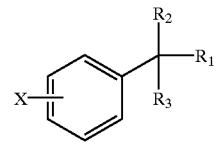

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313,692 to Bossinger, et al (hereby incorporated by reference) by administering a compound of the formula:

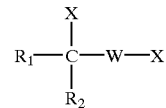

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

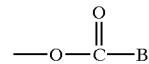

in which B represents an organic amine radical of the group consisting of heterocyclic, ureido and hydrazino radicals and the radical $-N(R_3)_2$ wherein $R_3$ represents hydrogen or an alkyl radical containing less than 4 carbon atoms.

Optically pure forms of halogen substituted 2-phenyl-1,2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

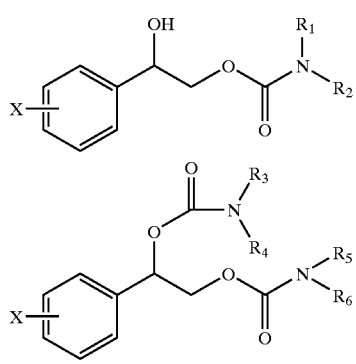

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

Halogen substituted 2-phenyl-1,2-ethanediol carbamate compounds of Formula (I) or Formula (II) have not been previously described as useful for the treatment of pain. Recent preclinical studies have revealed previously unrecognized pharmacological properties which suggest that a compound of Formula (I) or Formula (II) is useful in the treatment of pain. Therefore, it is an object of the present invention to teach a method for use of a compound of Formula (I) or Formula (II) in the treatment of pain.

SUMMARY OF THE INVENTION

The present invention is directed to a method for the treatment of pain comprising administering to a subject in need thereof a therapeutically effective amount of a compound selected from the group consisting of Formula (I) and Formula (II):

Formula (I)

Formula (II)

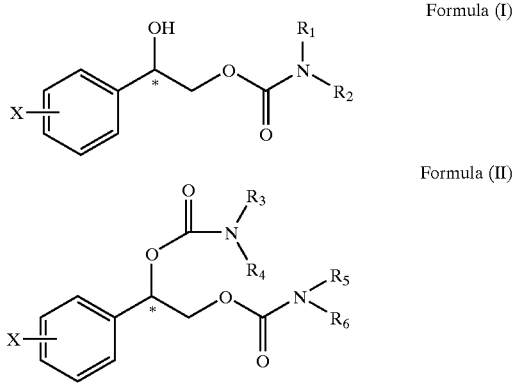

wherein
phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

Embodiments of the invention include a method for the treatment of pain comprising administering to a subject in need thereof a therapeutically effective amount of a pharmaceutical composition comprising a pharmaceutically acceptable carrier and a compound selected from the group consisting of Formula (I) and Formula (II).

Embodiments of the invention include the use of a compound selected from the group consisting of Formula (I) and Formula (II) for the preparation of a medicament for the treatment of pain in a subject in need thereof.

Embodiments of the method include the use of an enantiomer selected from the group consisting of Formula (I) and Formula (II) or enantiomeric mixture wherein one enantiomer selected from the group consisting of Formula (I) and Formula (II) predominates. For enantiomeric mixtures wherein one enantiomer selected from the group consisting of Formula (I) and Formula (II) predominates, preferably, one enantiomer selected from the group consisting of Formula (I) and Formula (II) predominates to the extent of about 90% or greater. More preferably, one enantiomer selected from the group consisting of Formula (I) and Formula (II) predominates to the extent of about 98% or greater.

DETAILED DESCRIPTION OF THE INVENTION

The present invention is directed to a method for the treatment of pain comprising administering to a subject in need thereof a therapeutically effective amount of a compound selected from the group consisting of Formula (I) and Formula (II):

Formula (I)

Formula (II)

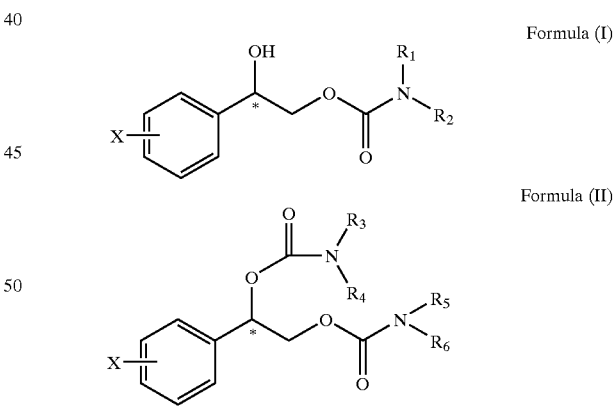

wherein
phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of a compound selected from the group consisting of Formula (I) and Formula (II) wherein X is chlorine; preferably, X is substituted at the ortho position of the phenyl ring.

The present method also includes the use of a compound selected from the group consisting of Formula (I) and Formula (II) wherein $R_1$, $R_2$, $R_3$, $R_4$, $R_5$ and $R_6$ are preferably selected from hydrogen.

An embodiment of the present method includes the use of an enantiomer selected from the group consisting of Formula (I) and Formula (II) or enantiomeric mixture wherein one enantiomer selected from the group consisting of Formula (I) and Formula (II) predominates wherein X is chlorine; preferably, X is substituted at the ortho position of the phenyl ring.

The present method also includes the use of an enantiomer selected from the group consisting of Formula (I) and Formula (II) or enantiomeric mixture wherein one enantiomer selected from the group consisting of Formula (I) and Formula (II) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (I) and Formula (II) predominates, preferably, an enantiomer selected from the group consisting of Formula (I) and Formula (II) predominates to the extent of about 90% or greater. More preferably, an enantiomer selected from the group consisting of Formula (I) and Formula (II) predominates to the extent of about 98% or greater.

An embodiment of the present method includes the use of an enantiomer selected from the group consisting of Formula (Ia) and Formula (IIa) or enantiomeric mixture wherein one enantiomer selected from the group consisting of Formula (Ia) and Formula (IIa) predominates:

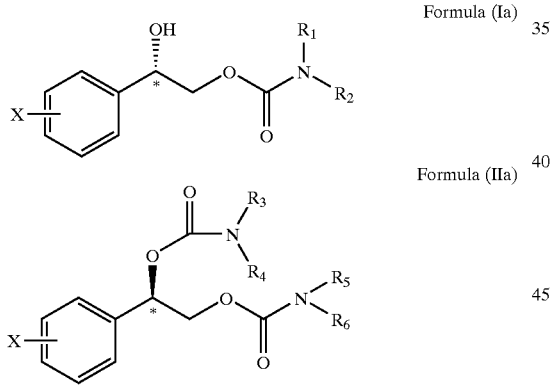

Formula (Ia)

Formula (IIa)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of an enantiomer selected from the group consisting of Formula (Ia) and Formula (IIa) or enantiomeric mixture wherein one enantiomer selected from the group consisting of Formula (Ia) and Formula (IIa) predominates wherein X is chlorine; preferably, X is substituted at the ortho position of the phenyl ring.

The present method also includes the use of an enantiomer selected from the group consisting of Formula (Ia) and Formula (IIa) or enantiomeric mixture wherein one enantiomer selected from the group consisting of Formula (Ia) and Formula (IIa) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (Ia) and Formula (IIa) predominates, preferably, an enantiomer selected from the group consisting of Formula (Ia) and Formula (IIa) predominates to the extent of about 90% or greater. More preferably, an enantiomer selected from the group consisting of Formula (Ia) and Formula (IIa) predominates to the extent of about 98% or greater.

An embodiment of the present method includes a method for the treatment of pain comprising administering to a subject in need thereof a therapeutically effective amount of an enantiomer selected from the group consisting of Formula (Ib) and Formula (IIb) or enantiomeric mixture wherein one enantiomer selected from the group consisting of Formula (Ib) and Formula (IIb) predominates:

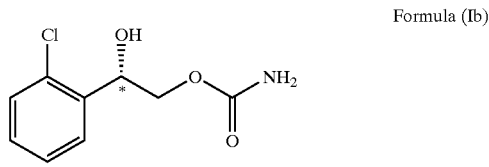

Formula (Ib)

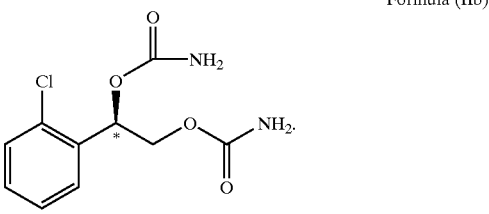

Formula (IIb)

For enantiomeric mixtures wherein one enantiomer selected from the group consisting of Formula (Ib) and Formula (IIb) predominates, preferably, an enantiomer selected from the group consisting of Formula (Ib) and Formula (IIb) predominates to the extent of about 90% or greater. More preferably, an enantiomer selected from the group consisting of Formula (Ib) and Formula (IIb) predominates to the extent of about 98% or greater.

Other crystal forms of the present invention may exist and as such are intended to be included in the present invention.

It is apparent to those skilled in the art that the compounds of the invention are present as racemates, enantiomers and enantiomeric mixtures thereof. A carbamate enantiomer selected from the group consisting of Formula (I), Formula (II), Formula (Ia), Formula (IIa), Formula (Ib) and Formula (IIb) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for the treatment of pain in a subject in need thereof. Examples of pain include, and are not limited to, pain that is centrally mediated, pain that is peripherally mediated, pain that is caused by structural tissue injury, pain that is caused by soft tissue injury or pain that is caused by progressive disease. Centrally mediated, peripherally mediated, structural tissue injury, soft tissue injury or progressive disease related pain include acute pain or chronic pain.

Acute pain includes pain caused by acute injury, trauma, illness or surgery (for example, open-chest surgery (including open-heart or bypass surgery)). Acute pain also includes, and is not limited to, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

An example of the method of the present invention comprises administering to the subject a therapeutically effective amount of a compound selected from the group consisting of Formula (I) and Formula (II) in a pharmaceutical composition comprising a pharmaceutically acceptable carrier and a compound selected from the group consisting of Formula (I) and Formula (II). The method of the present invention also includes the use of a compound selected from the group consisting of Formula (I) and Formula (II) for the preparation of a medicament for the treatment of pain.

Another example of the method of the present invention comprises administering to the subject a therapeutically effective amount of a compound selected from the group consisting of Formula (I) and Formula (II) or a pharmaceutical composition thereof in combination with one or more agents useful in the treatment of pain.

A compound selected from the group consisting of Formula (I) and Formula (II) or pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of a compound selected from the group consisting of Formula (I) and Formula (II) or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration) and the use of a particular compound of Formula (I) or Formula (II) or pharmaceutical composition thereof.

Optimal dosages to be administered may be readily determined by those skilled in the art and will result in the need to adjust the dose to an appropriate therapeutic level. The use of either daily administration or post-periodic dosing may be employed. Preferably, a compound of Formula (I) or Formula (II) or pharmaceutical composition thereof for the treatment of pain is administered orally or parenterally.

In accordance with the methods of the present invention, a compound of Formula (I) or Formula (II) or pharmaceutical composition thereof described herein may be administered separately, at different times during the course of therapy or concurrently in divided combination or single combination forms. Advantageously, a compound selected from the group consisting of Formula (I) and Formula (II) or pharmaceutical compositions thereof may be administered in a single daily dose or the total daily dosage may be administered via continuous delivery or in divided doses of two, three or four times daily. The instant invention is therefore to be understood as embracing all such methods and regimes of continuous, simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, a compound of Formula (I) or Formula (II) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition. Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

Preferably, a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

Biological Experimental Example

The activities of a compound of Formula (I) and Formula (II) for use in the treatment of pain were evaluated in the following experimental example which is intended to be a way of illustrating but not limiting the invention.

Bennett Model (Chronic Constrictive Injury)

The Bennett model consists of sciatic nerve loose ligation in rats (Bennett G J and Xie Y K, A peripheral mononeuropathy in rat that produces disorders of pain sensation like those seen in man, *Pain*, 1988, 33, 87–107). Although the pharmacological profile of the spontaneous pain, protective posture and allodynia (minor) is similar to that of clinical neuropathic pain, the loose chronic ligature of sciatic nerve in the Bennett model causes greater thermal hyperalgesia than mechanical allodynia due to its inflammatory mechanism. The loose ligation causes the constriction/swelling followed by inflammation at the ligation site, a condition most commonly associated with various types of pain. The behavioral response to the ligature is one of hyperalgesia. Thus, anti-hyperalgesia reduces chronic signs of pain hypersensitivity. Therefore, the Bennett model is used to evaluate antinociceptive pain (Cui J G, Possible role of inflammatory mediators in tactile hypersensitivity in rat models of mononeuropathy, *Pain*, 2000, 88 (3), 239–248; Lovell J A, Changes in Spinal Serotonin Turnover Mediate Age-Related Differences in the Behavioral Manifestations of Peripheral Nerve Injury, *Pharmacol. Biochem. Behav.*, 2000, 66 (4), 873–878; Yasuda T, The novel analgesic compound OT-7100[5-n-butyl-7-(3,4,5-trimethoxybenzoylamino) pyrazolo[1,5a]pyrimidine] attenuates mechanical nociceptive responses in animal models of acute and peripheral neuropathic hyperalgesia, *J. Pharmacol.*, 1999, 79 (1), 65–73; Toda K, Antinociceptive effects of neurotropin in a rat model of painful peripheral mononeuropathy, *Life Sci.*, 1998, 62 (10), 913–921; Munglani R, Neuropeptide changes persist in spinal cord despite resolving hyperalgesia in a rat model of mononeuropathy, *Brain Res.*, 1996, 743, 1 (2), 102–108).

An enantiomer of Formula (Ib) and Formula (IIb) were evaluated in the Bennett model for their efficacy in pain conditions at 3 doses (10, 30, and 100 mg/kg, p.o., n=8 animals per treatment). The anti-hyperalgesia effect was assessed at 30, 60, and 90 minutes after the oral administration.

Rats (180–220 g body weight) were anesthetized (sodium pentobarbital, 40 mg/kg, ip) and an incision was made at the mid-thigh level to expose the common left sciatic nerve. Four ligatures spaced 1 mm apart were loosely tied around the sciatic nerve. The wound was then sutured. The rats received an i.m. injection of 50,000 IU Penicillin and were allowed to recover after this procedure. At least one week after the surgery, when the chronic state was fully established, rats were consecutively submitted to thermal stimulation of both the non-lesioned and the lesioned hindpaws. The apparatus (UgoBasil, Reference: 7371) consists of 6 individual Plexiglas boxes (17×13×13 cm) placed upon an elevated glass floor. The rat was placed in the box and allowed to habituate for 10 minutes. A mobile infrared radiant source (setting 20) was then focused under the non-lesioned and lesioned hind-paws and the paw-withdrawal latencies in seconds were automatically recorded. The test was performed in a blinded fashion. The increased latency in treated animals as compared to control animals (those receiving only vehicle) was expressed as % of effectiveness of the drug. Data were analyzed by comparing the treated lesion group with controls using unpaired Student's t-test.

The results listed in Table 1 show that enantiomers of Formula (Ib) and Formula (IIb) have an anti-hyperalgesic effect against a thermal stimulation challenge (**represents a p value of <0.01, wherein the % change indicates the effectiveness of an enantiomer of Formula (Ib) and Formula (IIb) relative to a vehicle control).

TABLE 1

| Dose | Antihyperalgesic Effectiveness (% Effective) | | | | | |
|---|---|---|---|---|---|---|
| | 30 min | | 60 min | | 90 min | |
| (mg/kg) | (Ib) | (IIb) | (Ib) | (IIb) | (Ib) | (IIb) |
| 10 | — | — | 79 | 121 | 53 | 50 |
| 30 | 59 | 61 | 109 | 318** | 107 | 182** |
| 300 | 43 | 48 | 314** | 198** | 151 | 69 |

While the foregoing specification teaches the principles of the present invention, with examples provided for the purposes of illustration, it will be understood that the practice of the invention encompasses all of the usual variations, adaptations and/or modifications as come within the scope of the following claims and their equivalents.

What is claimed is:

1. A method for the treatment of pain comprising administering to a subject in need thereof a therapeutically effective amount of a compound selected from the group consisting of Formula (I) and Formula (II):

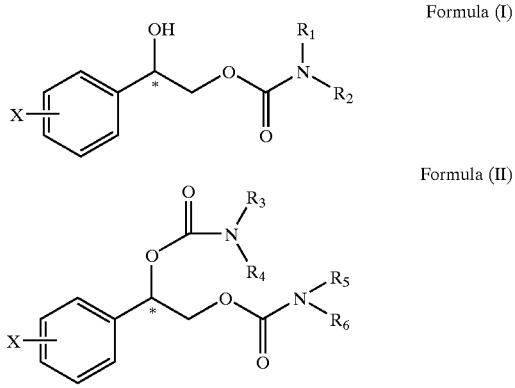

Formula (I)

Formula (II)

wherein
phenyl is substituted at X with one to five halogen atoms selected from the group consisting of fluorine, chlorine, bromine and iodine; and,
$R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. The method of claim 1 wherein X is chlorine.

3. The method of claim 1 wherein X is substituted at the ortho position of the phenyl ring.

4. The method of claim 1 wherein $R_1$, $R_2$, $R_3$, $R_4$, $R_5$ and $R_6$ are selected from hydrogen.

5. A method for the treatment of pain comprising administering to a subject in need thereof a therapeutically effective amount of an enantiomer selected from the group consisting of Formula (I) and Formula (II) or enantiomeric mixture wherein one enantiomer selected from the group consisting of Formula (I) and Formula (II) predominates:

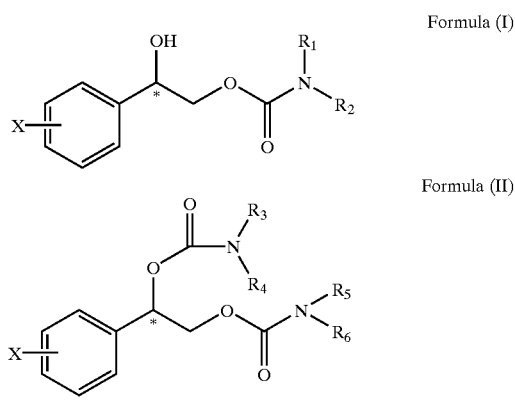

Formula (I)

Formula (II)

wherein
phenyl is substituted at X with one to five halogen atoms selected from the group consisting of fluorine, chlorine, bromine and iodine; and,
$R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

6. The method of claim 5 wherein X is chlorine.

7. The method of claim 5 wherein X is substituted at the ortho position of the phenyl ring.

8. The method of claim 5 wherein $R_1$, $R_2$, $R_3$, $R_4$, $R_5$ and $R_6$ are selected from hydrogen.

9. The method of claim 5 wherein one enantiomer selected from the group consisting of Formula (I) and Formula (II) predominates to the extent of about 90% or greater.

10. The method of claim 5 wherein one enantiomer selected from the group consisting of Formula (I) and Formula (II) predominates to the extent of about 98% or greater.

11. The method of claim 5 wherein the enantiomer selected from the group consisting of Formula (I) and Formula (II) is an enantiomer selected from the group consisting of Formula (Ia) and Formula (IIa):

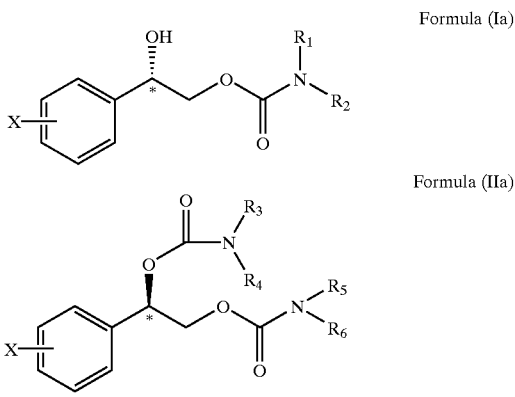

Formula (Ia)

Formula (IIa)

wherein
phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

12. The method of claim 11 wherein X is chlorine.

13. The method of claim 11 wherein X is substituted at the ortho position of the phenyl ring.

14. The method of claim 11 wherein $R_1$, $R_2$, $R_3$, $R_4$, $R_5$ and $R_6$ are selected from hydrogen.

15. The method of claim 11 wherein one enantiomer selected from the group consisting of Formula (Ia) and Formula (IIa) predominates to the extent of about 90% or greater.

16. The method of claim 11 wherein one enantiomer selected from the group consisting of Formula (Ia) and Formula (IIa) predominates to the extent of about 98% or greater.

17. The method of claim 5 wherein the enantiomer selected from the group consisting of Formula (I) and Formula (II) is an enantiomer selected from the group consisting of Formula (Ib) and Formula (IIb):

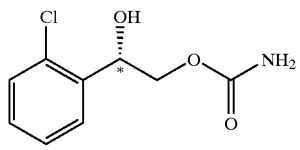

Formula (Ib)

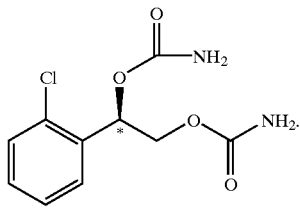

Formula (IIb)

18. The method of claim 17 wherein one enantiomer selected from the group consisting of Formula (Ib) and Formula (IIb) predominates to the extent of about 90% or greater.

19. The method of claim 17 wherein one enantiomer selected from the group consisting of Formula (Ib) and Formula (IIb) predominates to the extent of about 98% or greater.

20. The method as in claim 1 wherein pain is selected from pain that is centrally mediated, pain that is peripherally mediated, pain that is caused by structural tissue injury, pain that is caused by soft tissue injury or pain that is caused by progressive disease.

21. The method as in claim 1 wherein pain is selected from acute pain or chronic pain.

22. The method of claim 21 wherein acute pain is selected from pain caused by acute injury, trauma, illness or surgery.

23. The method of claim 22 wherein surgery is open-chest surgery selected from open-heart or bypass surgery.

24. The method of claim 21 wherein acute pain is selected from post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

25. The method of claim 21 wherein chronic pain is selected from pain caused by an inflammatory condition, osteoarthritis, rheumatoid arthritis or as sequela to disease, acute injury or trauma.

26. The method of claim 21 wherein chronic pain is selected from upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

27. The method as in claim 1 wherein the therapeutically effective amount is from about 0.01 mg/Kg/dose to about 100 mg/Kg/dose.

* * * * *